United States Patent
Izraelev

(10) Patent No.: US 6,861,778 B2
(45) Date of Patent: Mar. 1, 2005

(54) SYSTEM FOR PASSIVE AND STABLE SUSPENSION OF A ROTOR IN ROTOR/STATOR ASSEMBLIES

(76) Inventor: Valentin M. Izraelev, 6574 Cherokee Trail West, Eden Prairie, MN (US) 55344

( * ) Notice: Subject to any disclaimer, the term of this patent is extended or adjusted under 35 U.S.C. 154(b) by 70 days.

(21) Appl. No.: 10/376,875

(22) Filed: Feb. 28, 2003

(65) Prior Publication Data

US 2004/0174079 A1 Sep. 9, 2004

(51) Int. Cl.[7] .................................................. H02K 7/09
(52) U.S. Cl. ....................................... 310/90.5; 623/3.14
(58) Field of Search ........................ 310/90.5; 417/356, 417/420; 623/3.14

(56) References Cited

U.S. PATENT DOCUMENTS

| | | | |
|---|---|---|---|
| 3,470,828 A | 10/1969 | Powell, Jr. et al. | 104/148 |
| 4,382,245 A | 5/1983 | Harrigan | 335/306 |
| 4,688,998 A * | 8/1987 | Olsen et al. | 417/356 |
| 4,944,748 A * | 7/1990 | Bramm et al. | 623/3.14 |
| 5,055,005 A * | 10/1991 | Kletschka | 417/356 |
| 5,177,387 A | 1/1993 | McMichael et al. | 310/90.5 |
| 5,195,877 A * | 3/1993 | Kletschka | 417/356 |
| 5,302,874 A * | 4/1994 | Pinkerton | 310/90.5 |
| 5,345,128 A | 9/1994 | Pinkerton et al. | 310/90.5 |
| 5,404,062 A | 4/1995 | Hones et al. | 310/90.5 |
| 5,470,208 A * | 11/1995 | Kletschka | 417/356 |
| 5,471,105 A | 11/1995 | Clifton et al. | 310/90.5 |
| 5,495,221 A | 2/1996 | Post | 335/299 |
| 5,508,573 A | 4/1996 | Andrews et al. | 310/90.5 |
| 5,685,700 A * | 11/1997 | Izraelev | 417/423.7 |
| 5,789,837 A | 8/1998 | Shin et al. | 310/90.5 |
| 5,847,480 A | 12/1998 | Post | 310/90.5 |
| 5,924,848 A * | 7/1999 | Izraelev | 417/420 |
| 5,938,412 A * | 8/1999 | Izraelev | 417/423.7 |
| 6,206,659 B1 | 3/2001 | Izraelev | 417/420 |
| 6,304,015 B1 | 10/2001 | Filatov et al. | 310/90.5 |
| 6,547,539 B2 | 4/2003 | Izraelev | 417/423.1 |

FOREIGN PATENT DOCUMENTS

FR      2828915 A1 *   2/2003     F16C/32/04

* cited by examiner

Primary Examiner—Joseph Waks
(74) Attorney, Agent, or Firm—Haugen Law Firm PLLP

(57) ABSTRACT

A rotary mechanism includes a stator body defining a chamber and an elongated rotor operationally disposed within the chamber. The elongated rotor has opposed ends with a central axis defining an axis of rotation, with magnetic driven elements disposed on the rotor and positioned outwardly of the rotor axis between the opposed ends. Passive magnetic bearing pairs are positioned along opposed ends of the rotor body with each bearing pair being similarly polarized so as to be in mutually attracting or mutually repelling relationship. A third passive magnetic bearing pair is positioned along the rotor axis between the opposed ends with the third bearing pair being magnetically coupled similarly to the first and second bearing pairs, with the passive magnetic bearings creating an unstable negative force in a plane perpendicular to the axis of rotation of the rotor with the negative stiffness being overcome upon rotation of the rotor creating a centrifugal force of a magnitude greater than that of the unstable negative force.

7 Claims, 3 Drawing Sheets

SYSTEM FOR PASSIVE AND STABLE SUSPENSION OF A ROTOR IN ROTOR/STATOR ASSEMBLIES

BACKGROUND OF THE INVENTION

The present invention relates generally to a novel suspension system for the rotor component in a rotor/stator assembly, and more particularly to such a system which provides for passive and stable suspension of the rotor. Assemblies utilizing the features of the present invention are adapted for a wide variety of applications, including fluid handling systems for fragile or aggressive fluids, as well as for other applications pertaining to instrumentation, as well as applications for such assemblies which may be characterized as either delicate and/or rugged. The novel passive and stable suspension system of the present invention includes a rotor which is typically suspended within a stator, with the rotor being stabilized through passive magnetic as well as hydrodynamic forces.

The magnetic components may be designed in a variety of different coupling arrangements, with passive magnetic bearings being employed for creating stability along certain selected planes or axes and further creating one resultant unstable negative force in one plane or along an axis. More specifically, the magnetic forces are designed to create an unstable negative force in a plane perpendicular to the axis of rotation of the rotor, with stable and positive forces and moments being created in all other degrees of freedom excepting of course, rotation of the rotor. This resultant instability in the axis of rotation is overcome upon rotation of the rotor creating a centrifugal force of magnitude greater than that of the unstable negative force. In other words, when rotating, the forces created in the rotor return the body to an appropriate point of origin for the intersection of the X, Y and Z axes.

The suspension system of the present invention utilizes magnetic bearings for creation of positive stiffness and a resultant negative stiffness, with the overall stiffness in five of the six degrees of freedom being positive. Dynamic stability of the system is ultimately achieved through centrifugal/centripital forces, with dynamic stability being achieved.

Except for the passive magnetic stabilization system and the dynamic magnetic forces utilized to drive the rotor, assemblies of the present invention are otherwise bearing and seal-free. Passive magnetic forces are applied to the rotor during periods of rotation and dwell, with these passive forces including a resultant unstable negative force in a plane or along an axis perpendicular to the axis of rotation. As such, assemblies employing the magnetically stabilized rotor/stator assemblies of the present invention are particularly well adapted for a wide variety of mechanical applications, with one such application being in a centrifugal pump for handling highly aggressive such as corrosive, poisonous, or dangerously radioactive fluids, as well as fragile fluids including human or animal blood. During any transfer/movement of such fluids, it is frequently dangerous to expose the structure to forces such as unusual impact and/or shear forces, and thus the advantage of utilizing bearing and seal-free pumps, and particularly one wherein the rotor/stator assembly is at least partially magnetically stabilized. A particular advantageous feature of the present invention is that of providing a passive magnetic force to the rotor which when combined with the centrifugal forces, reduces and/or completely eliminates surface-to-surface contact between rotor and stator surfaces.

In connection with one application of the present invention, pump assemblies utilizing the features of the present invention may be exposed to aggressive fluids, including corrosion, poisonous or radioactive fluids, as well as fluids which cannot tolerate contamination. Through elimination of seals and/or bearings the lifetime and/or longevity of the pump or other assembly or structure is increased.

Poisonous fluids, for example, become extremely dangerous whenever leakage develops, a common consequence of bearing failure. In pump applications for the present invention, a rotor or impeller is utilized in an assembly which is bearing and seal-free, with the rotor being dynamically balanced and stable during operation. Bearing and seal-free pumps utilizing the rotor/stator assemblies of the present invention are particularly well adapted for transferring human blood and other delicate liquids without damaging and/or otherwise significantly adversely affecting their composition or quality. Furthermore, the magnetic stabilization feature of the present invention provides stable positioning of the rotor during operation. Depending upon the application, the rotor may be fabricated from any of a variety of non-magnetic materials, including, for example, metals such as titanium and non-metals such as pyrolytic carbon. Certain engineered plastics have also been found useful.

Another feature of rotors and stators suitable for application in the present invention is that they be capable of receiving and reliably retaining passive magnetic components which deliver forces stabilizing the rotor. Although not in the form of a mechanical surface-contacting bearing, the passive magnetic components utilized in the present invention may be positioned and/or arranged to function as magnetic thrust bearings. The rotor is also arranged to be capable of receiving and reliably retaining magnetic components such as electromagnetic components used in the drive system for delivering energy to the rotor for rotation. Generally, an array of permanent magnets are positioned within the rotor and stator components in a brushless motor configuration. Alternatively, the drive mechanism may employ permanent magnet-to-permanent magnet couplings similarly mounted. The arrangement of the present invention provides for the economic utilization of a magnetically levitated rotor/stator assembly which may be fabricated by conventional processes, and therefore highly economically viable. Rotor stabilization and/or suspension may be achieved with passive magnetic bearings such as positioned in different arrangements or configurations. In preferred configurations, magnetically coupled bearings may provide positive forces in five of the six possible degrees of freedom, while providing one unstable negative force, preferably in a plane perpendicular to the axis of rotation, with this instability being overcome by a centrifugal force of greater magnitude.

GENERAL COMMENTARY

An English scientist, Rev. Samuel Earnshaw concluded in his paper published in 1839 that it is impossible to create a passive stable suspension of a body using passive electromagnetic and electrostatic forces. Following Earnshaw's theory and utilizing stable suspension or levitation, active magnetic bearings including permanent magnets and coils have been utilized to control and/or manipulate one or more degrees of freedom. Alternatively, superconductors may be utilized instead of magnetic bearings, however means for achieving a result appear impractical. Active magnetic bearing technology functions, but it has been found complex, costly, and less reliable than other mechanical means. In certain applications, active magnetic bearings are substituted by a combination of hydrodynamic and mechanical journal bearings, but in such cases, it is not a true suspension since clearances between the rotor and the journal are tight, frequently in the range of between 4 and 12 microns, although slightly greater tolerance levels may be satisfactorily utilized in certain applications.

When an object such as a rotor rotates in a liquid fluid medium, the rotor and the medium interact and inertial centrifugal/centripital forces are created. These forces are governed by the following equation:

$$F_c = \Delta\rho(W^2)(R_c)(V)$$

wherein:

$F_c$=centrifugal force acting on the rotor in the direction perpendicular to the axis of rotation;

$\Delta\rho$=difference in the density of the rotor and the liquid;

W=angular velocity of excursion of the rotor axis of rotation;

$R_c$=radius of excursion of the rotor axis of rotation; and

V=volume of the rotor.

When the density of the rotor is less than that of the liquid medium, the resultant inertial force $F_c$ acting on the rotor is directed toward the axis of rotation and is a source of creation of positive stiffness for the rotor suspension in two degrees of freedom perpendicular to the axis of rotation. For the rotor 12 in FIG. 1, these two degrees of freedom are displacements in the X and Y directions.

In certain applications, the passive and stable suspension of the rotor may be achieved by utilizing those hydrodynamic and inertial forces developed in rotation of the liquid and the rotor. Since the centrifugal force $F_c$ is dependent upon the square of the rate of rotation, stable passive levitation is achieved only after reaching a predetermined level of rate of rotation.

In other applications, the less dense rotor effect may be used in combination with non-contact bearings, namely passive magnetic bearings. In these instances, the positive stiffness created by centrifugal forces becomes greater than the resultant negative stiffness of the passive permanent magnet system created in the same plane. Thus, the stable suspension of the rotor may be achieved. Thus, the centrifugal forces developed in operation of the assembly of the present invention overpower those forces of instability considered by Earnshaw in his conclusion.

In the present arrangement, it will be appreciated that passive and stable suspension of the rotor may be obtained with the rotor being of a selected density, less than the density of the medium in which it rotates. This passive and stable suspension is achieved with permanent magnet pairs configured to provide permanent magnet bearings, and with the rotor having its selected density of less than that of the medium in which it is rotated. In each instance, the rotor is driven by non-contact means, such as a magnetic assembly in a brushless motor configuration.

In the present arrangement, centrifugal/centripital forces in combination with magnetic forces overcome any instability in the X, Y and Z axes. The ratios of positive and any resultant negative stiffness of magnetic bearings are such that overall positive stiffness of the rotor assembly is achieved through all five degrees of rotor freedom aided by centrifugal/centripital forces developed in the rotating fluid/medium. The rotor is therefore rendered stably suspended in the medium when the restoring forces from positive stiffnesses of the system in the respective degrees of freedom are greater than external destabilizing forces of negative stiffness.

SUMMARY OF THE INVENTION

Therefore, it is a primary object of the present invention to provide a passive and stable suspension of a rotor utilizing magnetic or electrostatic forces applied relative to a reference frame.

It is a further object of the present invention to provide a stable suspension of a rotor within a stator with positive stiffness in all five degrees of freedom, excepting in the sixth degree of freedom which is defined as a rotation around or about the axis of rotation of the rotor when a torque is applied.

It is a further object of the present invention to provide a passive and stable suspension of a rotor within a stator utilizing inertial dynamic interaction between the rotor and a fluid medium in which the rotor rotates to create positive stiffness in all five degrees of freedom of the rotor.

Yet a further object of the present invention is to provide a passive and stable suspension of the rotor incorporating passive permanent magnetic bearings and dynamic interaction between the rotor and a fluid medium in which the rotor is rotating for use in a variety of applications.

It is a further object of the present invention to provide a novel passive and stably suspended rotor in a one of a kind mechanism employing a rotor confined within a stator, and wherein stability is achieved through rotation of the rotor.

It is yet a further object of the present invention to provide a novel rotor/stator assembly preferably of generally cylindrical or other surface of revolution configuration wherein the rotor is disposed within the core of the stator, creating an annular zone between the chamber walls and the rotor surface, and wherein a fluid media fill is provided in the annular zone, and with forces being exerted or applied to the fluid media upon rotation of the rotor.

It is a further object of the present invention to provide a rotor/stator assembly wherein a fluid medium is contained in the stator chamber.

It is yet a further object of the present invention to provide a novel rotor/stator assembly wherein a fluid media flows into and out of the stator chamber.

Other and further objects of the present invention will become apparent to those skilled in the art upon a study of the following specification, appended claims, and accompanying drawings.

IN THE DRAWINGS

DESCRIPTION OF THE PREFERRED EMBODIMENT

Figure 1:
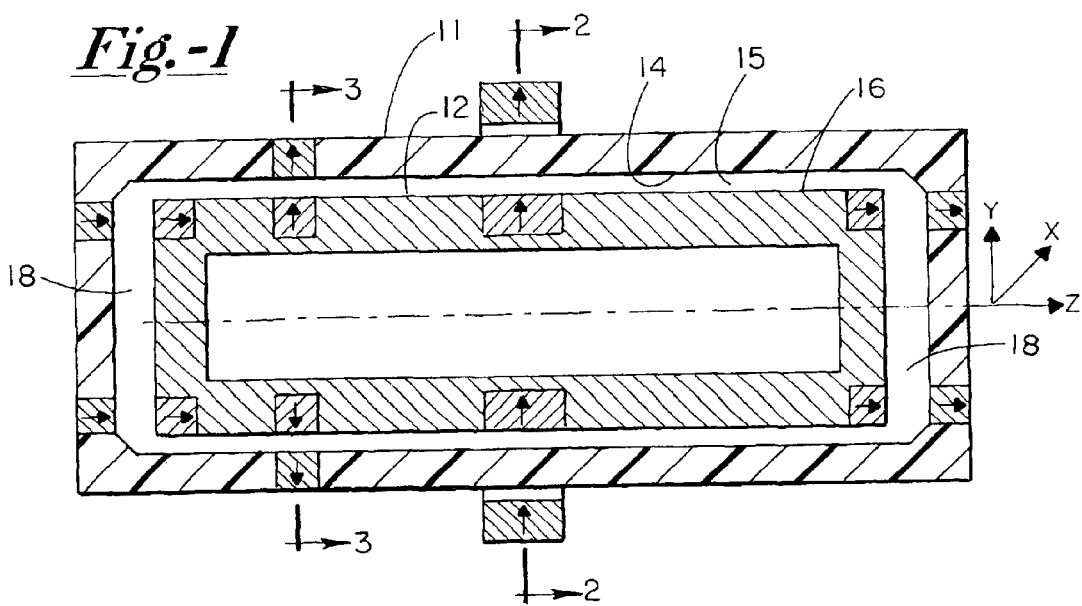
FIG. 1 is a sectional view taken through the diameter of a rotor/stator assembly and with portions of the stator being removed with polarity of the magnetic components being demonstratively indicated with arrows.
Figure 2:
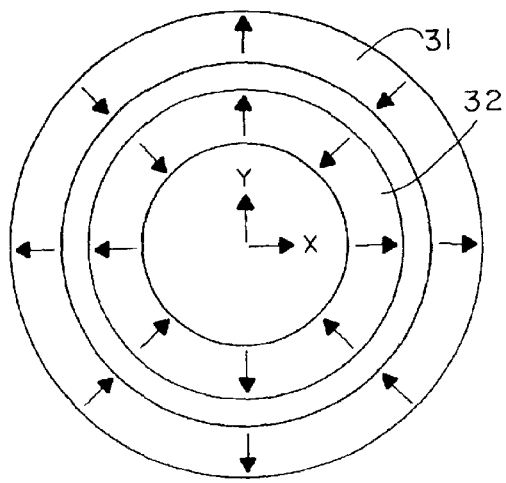
FIG. 2 is a view taken along the line and in the direction of the arrows 2—2 of FIG. 1 and illustrating one embodiment of a magnetic drive coupling arrangement, and with the polarity of the magnets being dynamically altered by electromagnetic means for creating relative rotation between rotor and stator.

With reference to the device illustrated in FIG. 1, the system generally designated 10 comprises a shell or housing 11 along with a rotor structure 12. Body 11 has an inner wall 14 which defines the chamber zone 15 therewithin. Rotor 12 has an outer surface as at 16 which is spaced from wall 14, thereby configuring chamber zone 15 into an annular zone. End zone openings 18—18 are provided which comprise faces or bases. The zones 15 and 18—18 are normally filled with media or fluid as indicated in FIG. 1. Rotor body 11 has six degrees of freedom in a Cartesian coordinate system, these degrees of freedom being manifested in forces delivered along coordinate axes and rotation about these axes.

The origin of the system is located in the geometrical center of the rotor 12. In rotor 12, one degree of freedom is preserved for rotation about the Z axis. Support of rotor 12 is provided, with the support having the positive stiffness in each of the other five degrees of freedom, with "positive stiffness" being defined as a restoring force created whenever displacement from the origin occurs. In other words, the restoring force created by centrifugal forces return the body to the origin, thus providing overall stability for the operational structure. "Negative stiffness", on the other hand, is a force moving or rotating the body from the origin. Applying this conclusion to the present circumstance, and using as an example, rotor 12, it would be concluded that rotor 12 cannot be stably suspended by applying only permanent (passive) magnets for all required degrees of freedom.

Figure 3:
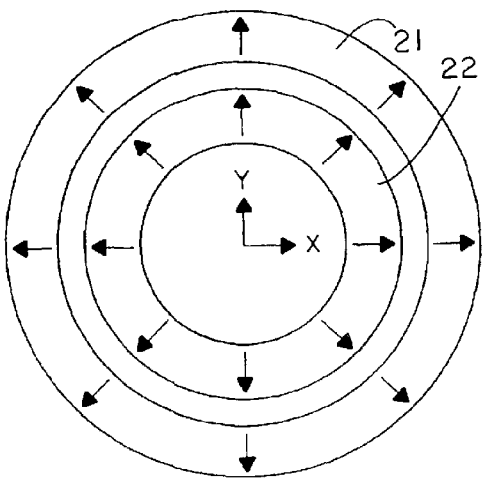
FIG. 3 is a view taken along the line and in the direction of the arrows 3—3 of FIG. 1 and illustrating an alternative embodiment of the relative arrangement of polarity of the magnetic bearing coupling.
Figure 5:
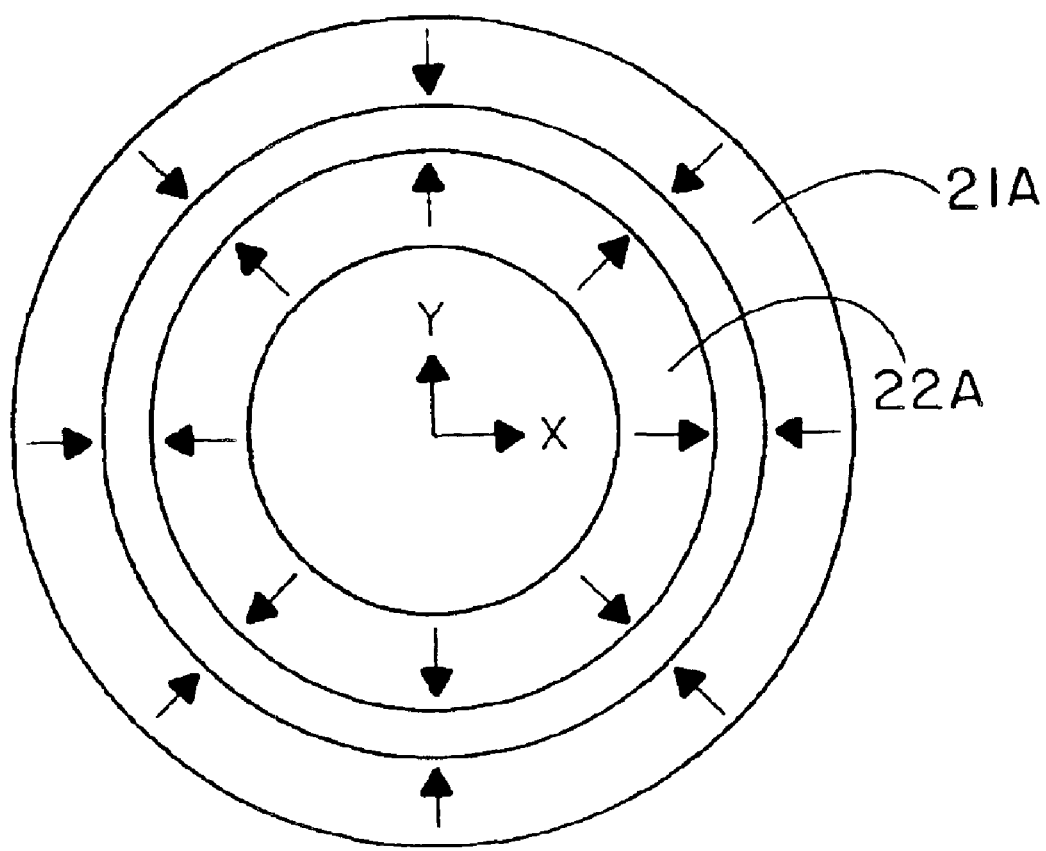
FIG. 5 is a view similar to FIG. 3 and illustrating an alternative magnetic bearing coupling arrangement utilizing modified arrangement of polarity, with this arrangement of polarity not being incorporated into the embodiment of FIGS. 1–4.

Depending upon the respective magnetization polarities of the passive magnet pairs 21 and 22 comprising a magnetic bearing for mounting in the stator and rotor, attractive or repulsive forces from permanent magnets comprising the bearing can be obtained. These are illustrated in FIGS. 3 and 5 respectively. Magnetization polarities, orientations, or directions are represented by arrows, with the attractive bearing in FIG. 3 being stable along the Z axis and unstable along X and Y axes. The magnetically repulsive bearing illustrated in FIG. 5 and comprising magnetic pairs 21A and 22A is stable in the direction of the X and Y axes, and unstable in the Z axis.

As illustrated in FIGS. 3 and 5, permanent magnet pairs 21–22, 21A–22A are each formed of respective hollow right cylinders, which have a coaxial hollow core. In other words, permanent magnet 21 is coaxially arranged with respect to permanent magnet 22, with the hollow core of cylindrical magnet 21 being substantially operationally aligned with the hollow core of cylindrical magnet 22 along the Z axis of system 10.

In addition to those forces created from the axially spaced permanent magnetic bearing pairs, additional stabilizing and destabilizing forces are created by the magnetic drive coupling utilized to cause relative rotation between rotor and stator components. Stated another way, when attractive forces are involved in the permanent magnet arrangement of FIG. 3, the system becomes stable in the axis of rotation, and when repulsive forces are utilized as in FIG. 5, then the system becomes unstable in the axis of rotation. In this connection, the numerical designations for components in FIG. 5 are identified with the suffix "a", and except for polarity, are the same as those components of FIG. 3.

Figure 4:
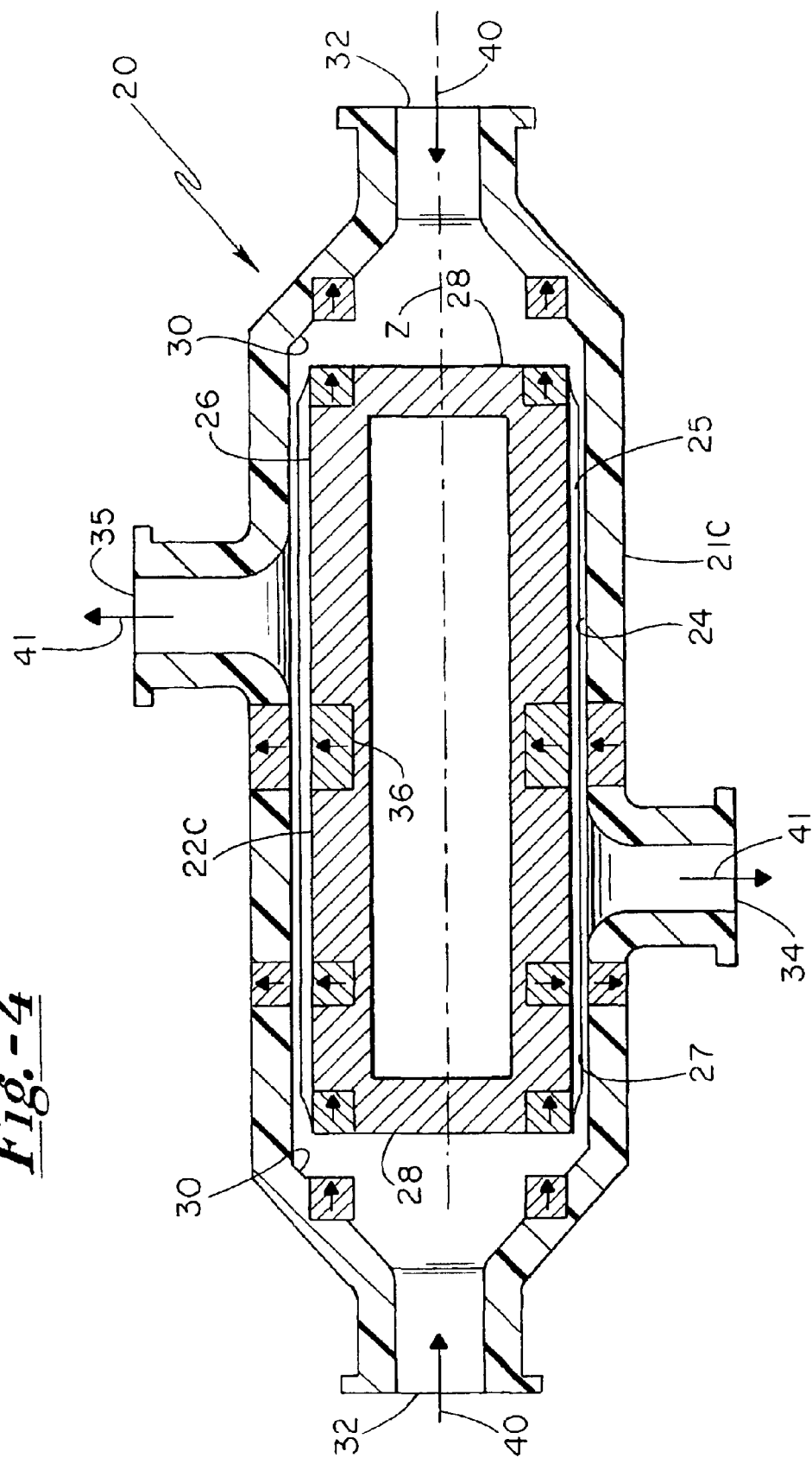
FIG. 4 is a view of a modified embodiment of the assembly of FIG. 1, and illustrating an arrangement of the present invention in a fluid pump configuration.

With attention now being directed to FIG. 4 of the drawings, the modified embodiment illustrated therein is in a drive housing configuration or system generally designated 20. System 20 comprises a shell or housing 21C along with a rotor structure 22C. Body 21C has an inner wall 24 which defines a chamber zone 25 therewithin. Rotor 22C has an outer surface as at 26 which may, in certain applications, be provided with elongated radially extending fins as at 27. The outer edges of fins 27 are spaced from wall 24 so as to define an annular gap or spacing therebetween. With rotor 22C having an outer surface as at 26, the chamber zone creates an annular opening. The end caps 28—28 of rotor 22C are closed, and spaced axially from inner ends 30—30 of housing or body 21C. Inlet ports such as provided at 32—32 along with a pair of symmetrically disposed outlet ports 34 and 35 may be provided when system 20 is designed to function as a pump. Ports 34 and 35 are disposed equal distance between the central transverse axis 36 of rotor 22C. Zones 25 and 28—28 are, of course, filled with the pumped media or fluid during operation, with the density of the media or fluid being greater than that of rotor 22C. During operation, the pumped fluid enters pump along the line and in the direction of the arrows 40—40, and exiting the line and in the direction of the arrows 41—41.

It will be appreciated, of course, that various modifications may be made in the preferred embodiment illustrated above, and these modifications may be made without actually departing from the spirit and scope of the present invention.

What is claimed is:

1. A rotary mechanism comprising a stator body with an inner wall defining a chamber having an axis and enclosing a liquid and having opposed ends disposed coaxially with said chamber, an elongated rotor having opposed first and second ends and being operationally disposed within said chamber and having a rotor axis defining an axis of rotation, magnetic driven means disposed on said elongated rotor and being positioned radially outwardly of said rotor axis generally medially of said first and second ends, electromagnetic drive means coupled to a source of energy and arranged along said stator body to deliver rotational driving energy to said rotor through said magnetic driven means; said rotor comprising;

(a) a rotor body having a relative density substantially less than that of said chamber liquid;

(b) a configuration defining an elongated surface of revolution with an axial length defined between said first and second ends; and with a diameter of said rotor body transverse to said axis of rotation being selected to provide a clearance between an outer surface of said rotor body and the inner wall of said stator body;

(c) said rotary mechanism having a plurality of passive magnetic bearing pairs, each bearing pair consisting of first and second magnetic bodies in mutually magnetically coupled relationship with the first magnetic bodies of each bearing pair being mounted on said elongated rotary body and with the second magnetic bodies of each bearing pair being mounted along the inner wall of said stator disposed adjacent to and in magnetically coupled relationship with respective first magnetic bodies to form said bearing pairs;

(d) each of said first and second magnetic bodies solely comprising a permanent magnet;

(e) each of said first and second magnetic bodies comprising each of said passive magnetic bearing pairs being polarized and positioned in mutually attracting or mutually repelling relationship so as to function as radial and/or thrust bearings;

(f) said plurality of passive magnetic bearing pairs being further arranged to form a passive suspension means for said elongated rotary body within said stator body, with said suspension means having negative stiffness only in directions perpendicular to the axis of rotation; and (g) said negative stiffness being of a magnitude such that centrifugal forces developed during rotation of said rotary body overcome said negative stiffness and create positive stiffness of said rotor suspension in all required degrees of freedom.

2. The rotor of claim 1 wherein said first and second magnetically coupled bodies of said plurality of magnetic bearing pairs are each in the form of a hollow right cylinder having a coaxial core.

3. The rotor of claim 1 wherein said rotary mechanism comprises a centrifugal pump and wherein said stator body has an inlet port at one end of said chamber and in substantial coaxial relationship therewith, and an outlet port disposed on the inner wall of said stator generally medially of the elongated axis of said chamber.

4. The rotor of claim 3 wherein the outer surface of said elongated rotary body has a plurality of radially extending ribs.

5. The rotor of claim 1 wherein said rotor body has a relative density substantially less than that of said chamber liquid and wherein said stator body comprises a completely closed structure defining an enclosure with contained liquid retained therein.

6. The rotor of claim 1 wherein said rotary mechanism comprises a fluid handling mechanism and wherein said stator body has inlet and outlet ports for accommodating fluid flow through the chamber formed within said stator body.

7. The rotor of claim 1 wherein selected of said second magnetic bodies of at least one passive magnetic bearing pair are operationally disposed in spaced apart relationship from said stator body.

* * * * *